United States Patent [19]

Sodervall et al.

[11] Patent Number: 5,395,651
[45] Date of Patent: Mar. 7, 1995

[54] DEPOSITION OF SILVER LAYER ON NONCONDUCTING SUBSTRATE

[75] Inventors: Billy V. Sodervall, Markaryd; Thomas Lundeberg, Lidingö both of Sweden

[73] Assignee: Ad Tech Holdings Limited, St. Heiler, Channel Islands

[21] Appl. No.: 897,614

[22] Filed: Jun. 10, 1992

Related U.S. Application Data

[63] Continuation of Ser. No. 630,333, Dec. 13, 1990, abandoned, which is a continuation of Ser. No. 347,016, May 4, 1989, abandoned.

[51] Int. Cl.$^6$ .............................................. C23C 26/00
[52] U.S. Cl. .................................... 427/304; 427/305; 427/306; 427/437; 427/443.1
[58] Field of Search .............. 427/304, 305, 306, 437, 427/443.1

[56] References Cited

U.S. PATENT DOCUMENTS

| | | |
|---|---|---|
| 1,281,262 | 10/1918 | Andres . |
| 1,557,234 | 10/1925 | Bechhold . |
| 1,557,235 | 10/1925 | Bechhold . |
| 1,642,089 | 9/1927 | Schreier . |
| 1,685,204 | 9/1928 | Schreier . |
| 1,691,755 | 11/1928 | Ruttner . |
| 2,283,883 | 5/1942 | Conconi . |
| 2,363,354 | 11/1944 | Peacock . |
| 2,421,079 | 5/1947 | Narcus . |
| 2,459,896 | 1/1949 | Schwarz . |
| 2,459,897 | 1/1949 | Schwarz . |

(List continued on next page.)

FOREIGN PATENT DOCUMENTS

| | | | |
|---|---|---|---|
| 100570 | 2/1984 | European Pat. Off. | ............ 427/304 |
| 0206024 | 12/1986 | European Pat. Off. . | |
| 0251783 | 1/1988 | European Pat. Off. . | |
| 0301717 | 2/1989 | European Pat. Off. . | |
| 0318258 | 5/1989 | European Pat. Off. . | |
| 0328421 | 8/1989 | European Pat. Off. . | |
| 0379269 | 7/1990 | European Pat. Off. . | |
| 0399096 | 11/1990 | European Pat. Off. . | |
| 0400349 | 12/1990 | European Pat. Off. . | |
| 7107441 | 2/1971 | Japan | ..................... 427/306 |
| 0000269 | 1/1981 | Japan | ................. 427/443.1 |
| 1015986 | 1/1986 | Japan | ..................... 427/304 |
| 1236250 | 6/1971 | United Kingdom | ................. 427/305 |
| 1237032 | 6/1971 | United Kingdom . | |
| WO81/02667 | 10/1981 | WIPO . | |
| 8102667 | 10/1981 | WIPO . | |
| WO89/01793 | 3/1989 | WIPO . | |

OTHER PUBLICATIONS

De Minjer et al. *J. Electrochem. Soc.* (1973) 120:1644–1650.
"Oligodynamic Metals" by I. B. Romans, chapter 24 of Antiseptics and Disinfectants.
"Trace Metals in the Environment": by Smith & Carson from vol. 2, Silver pp. 216–218 (1927).
"The Silver Catheter" by Nelse Ockerblad, Journal of Urology Aug. 1942, pp. 262–264.
Handbook of Chemistry and Physics, Forty–Fourth Ed., pp. 3428–3430 (1962).
T. Lundeberg, "Prevention of Catheter–Associated Urinary–Tract Infections By Use of Silver–Impregnated Catheters" letter to Lancet, Nov. 1986, p. 1031.

*Primary Examiner*—Shrive Beck
*Assistant Examiner*—Vi Duong Dang
*Attorney, Agent, or Firm*—Morrison & Foerster

[57] ABSTRACT

Metallic silver is deposited upon the surface of a non-conducting substrate using a multi-step wet deposition process. The surface is cleaned, and then activated in an aqueous solution containing stannous tin. The silver is deposited as a colloidal material from an aqueous solution of a silver-containing salt, a reduction agent that reduces the salt to form the metallic silver, and a deposition control agent that prevents the silver from nucleating throughout the solution. After the substrate is coated, the coating is stabilized in an aqueous solution of a salt of a metal from the platinum group or gold, dissolved in dilute hydrochloric acid. The process is particularly effective for depositing uniform films of 2 to 2000 Angstroms thickness, which strongly adhere to the substrate.

20 Claims, No Drawings

U.S. PATENT DOCUMENTS

| | | | |
|---|---|---|---|
| 2,602,757 | 7/1952 | Kantrowitz et al. | |
| 2,639,997 | 5/1953 | Drake | |
| 2,653,893 | 9/1953 | Romans | |
| 2,689,199 | 9/1954 | Pessel | |
| 2,702,253 | 2/1955 | Bergstrom | |
| 2,813,056 | 11/1957 | Davis et al. | |
| 2,813,059 | 11/1957 | Davis et al. | |
| 2,822,289 | 2/1958 | Millard | |
| 2,836,515 | 5/1958 | McNally | |
| 2,879,175 | 3/1959 | Umblia et al. | |
| 2,924,535 | 2/1960 | Schaefer | 427/443.1 |
| 2,947,282 | 8/1960 | Brown | |
| 3,092,552 | 6/1963 | Romans | |
| 3,184,376 | 5/1965 | Degoli | |
| 3,214,292 | 10/1965 | Edson | |
| 3,396,727 | 8/1968 | Mount | |
| 3,515,571 | 6/1970 | Levy | |
| 3,561,995 | 2/1971 | Wu et al. | |
| 3,598,127 | 8/1971 | Wepsic | |
| 3,657,003 | 4/1972 | Kenney | |
| 3,695,921 | 10/1972 | Shepherd et al. | |
| 3,699,956 | 10/1972 | Kitrilakis et al. | |
| 3,798,050 | 3/1974 | Franz et al. | |
| 3,841,881 | 10/1974 | Feldstein et al. | |
| 3,874,882 | 4/1975 | Gulla et al. | |
| 3,877,965 | 4/1975 | Broadbent et al. | |
| 3,880,580 | 4/1975 | Horowitz | 427/304 |
| 3,904,792 | 9/1975 | Gulla et al. | |
| 3,914,520 | 10/1975 | Hovey | |
| 3,932,694 | 1/1976 | Hamaguchi | 427/305 |
| 4,027,393 | 6/1977 | Ellis et al. | |
| 4,054,135 | 10/1977 | Crossley | |
| 4,054,139 | 10/1977 | Crossley | |
| 4,082,557 | 4/1978 | Pizzio | 427/306 |
| 4,091,128 | 5/1978 | Franz et al. | |
| 4,126,582 | 11/1978 | Diem et al. | |
| 4,128,671 | 12/1978 | Suggs | 427/304 |
| 4,144,361 | 3/1979 | Feldstein | 427/304 |
| 4,148,945 | 4/1979 | Bangs | 427/306 |
| 4,171,393 | 10/1979 | Donley et al. | |
| 4,180,602 | 12/1979 | Schiavone | |
| 4,181,759 | 1/1980 | Feldstein | |
| 4,181,760 | 1/1980 | Feldstein | |
| 4,228,201 | 10/1980 | Feldstein | |
| 4,237,229 | 12/1980 | Hartdegen et al. | |
| 4,253,463 | 3/1981 | Kim | |
| 4,269,625 | 5/1981 | Molenaar | |
| 4,348,429 | 9/1982 | McIntyre | 427/304 |
| 4,355,083 | 10/1982 | Feldstein | 427/305 |
| 4,362,779 | 12/1982 | Arsac | 427/304 |
| 4,374,876 | 2/1983 | El-Shazly et al. | |
| 4,404,197 | 9/1983 | Fox et al. | |
| 4,411,648 | 10/1983 | Davis et al. | |
| 4,419,390 | 12/1983 | Feldstein | |
| 4,483,688 | 11/1984 | Akiyama | |
| 4,539,234 | 9/1985 | Sakamoto et al. | |
| 4,542,169 | 9/1985 | Costerson | |
| 4,563,485 | 1/1986 | Fox et al. | |
| 4,564,361 | 1/1986 | Akiyama | |
| 4,568,570 | 2/1986 | Giesecke | 427/305 |
| 4,569,673 | 2/1986 | Tesi | |
| 4,581,028 | 4/1986 | Fox et al. | |
| 4,592,920 | 6/1986 | Murtfeldt | |
| 4,603,152 | 7/1986 | Laurin | |
| 4,612,337 | 9/1986 | Fox, Jr. et al. | |
| 4,639,382 | 1/1987 | Ponjee et al. | |
| 4,642,104 | 2/1987 | Sakamoto | |
| 4,668,532 | 5/1987 | Moisan | 427/98 |
| 4,677,143 | 6/1987 | Laurin et al. | |
| 4,725,314 | 2/1988 | Gulla et al. | |
| 4,734,296 | 3/1988 | Schramm | |
| 4,737,188 | 4/1988 | Bahls | 427/304 |
| 4,738,782 | 4/1988 | Yamauchi et al. | |
| 4,784,647 | 11/1988 | Gross | |
| 4,847,049 | 7/1989 | Yamamoto | |
| 4,849,223 | 7/1989 | Pratt | |
| 4,915,694 | 4/1990 | Conston et al. | |
| 4,933,178 | 6/1990 | Capelli | |
| 4,973,320 | 11/1990 | Brenner et al. | |

DEPOSITION OF SILVER LAYER ON NONCONDUCTING SUBSTRATE

This application is a continuation of application Ser. No. 07/630333, filed Dec. 13, 1990, now abandoned, which is a continuation of application Ser. No. 07/347016, filed May 4, 1989, abandoned.

BACKGROUND OF THE INVENTION

This invention relates generally to the deposition of silver films on nonconducting substrates, and, more particularly, to deposition of such films that are very thin.

Thin films of certain metals on nonconducting substrates can have important commercial applications. Thin films of conducting metals on transparent substrates are used in electronic display devices. Thin films can be used to reflect heat in solar shading or other solar devices, and to filter radiation from sunlight. A thin film can reduce the incidence of infection caused by a device that is introduced into the human body, when the film is coated onto the device before introduction into the body. Thin films are used in packaging as a vapor barrier coating. These applications are only illustrative of the thousands of uses of thin films, and are not limiting of their uses.

In one particular application, films of silver or silver-containing compounds are particularly effective in reducing microbial infection in the human body. U.S. Pat. No. 4,404,197 describes the use of silver-containing salts in reducing the likelihood of infection of burn victims. U.S. Pat. No. 4,581,028 describes the use of antimicrobial silver salts in implants, and U.S. Pat. No. 4,603,152 describes other such devices utilizing silver compounds to resist infection. U.S. Pat. Nos. 4,054,139 and 4,483,688 disclose the use of a pure silver metallic coating on medical devices to reduce the incidence of infection. Thus, it is well established that coatings of silver or silver compounds are effective in reducing the chances of infection caused by medical devices that are implanted or inserted into the body.

Although the value of using silver to avoid infection is well established, there is less knowledge as to effective approaches to the best approach to providing the silver on the surface. Electrodeposition might be used, but in most cases the medical instruments are made of nonconducting materials which cannot be readily coated electrolytically on a commercial scale, with a thin, adherent coating. The '139 patent suggests that coating "of the type deposited by electroless deposition" would be operable, but gives no details of operable processes. The '688 patent describes the use of large 300 mesh particulate silver to coat catheters.

Silver can be coated onto nonconducting substrates by electroless processes. One example is the process used to coat silver onto mirrors, but such coatings are comparatively thick. Another example is dry deposition techniques such as vapor deposition or sputtering, but these cannot be used to coat irregularly shaped substrates, or the insides of long bores.

Because silver can be toxic in some circumstances, and is expensive, it is preferable to coat the silver as a very fine layer onto the electrically nonconducting substrate. The coating should be strongly adherent to the substrate, because loss of the coating might result in infection or passage of the silver into the body. There are not presently known techniques for depositing silver onto various types of nonconducting substrates that permit the deposition of a very thin, but uniform, transparent layer of silver, on the order of 2 to 2000 Angstroms thick, produce a highly adherent layer with good mechanical properties, and are readily adapted to large scale commercial manufacturing of coated products.

There therefore exists a need for such a coating technology. The present invention fulfills this need, and further provides related advantages.

SUMMARY OF THE INVENTION

The present invention provides a process for depositing thin, uniform layers of silver onto a wide variety of nonconducting substrates. The silver layer is adherent and effective in various uses, including, for example, antimicrobial medical applications, barrier packaging, and optical filters. The process can be performed at ambient temperature or, at most, slightly elevated temperature, using conventional industrial chemical procedures. It is highly controllable and reproducible, producing virtually identical layers on large numbers of substrates. Tests have shown that the yields of good quality coated parts using the approach of the invention is very high.

In accordance with the invention, a process for depositing a uniform thin layer of silver onto the surface of an electrically non-conducting substrate comprises the steps of activating the surface in an aqueous activating solution containing at least about 0.001 grams per liter of a salt containing stannous tin ions; and depositing silver onto the surface from a deposition solution of a silver-containing salt, a reduction agent in a concentration sufficient to reduce the silver salt to form metallic silver at the surface of the substrate, and a deposition control agent in a concentration sufficient to prevent the silver in the solution from precipitating from the solution, and to permit it to deposit upon the surface of the substrate, the step of depositing being accomplished in darkness. If necessary, the surface of the substrate may be cleaned prior to processing. Preferably, the silver layer is stabilized after deposition, but before use.

The preferred approach deposits a thin, uniform layer of silver, preferably 2 to 2000 Angstroms thick, at the rate of about 5–7 Angstroms per second in the deposition solution. The thickness of the surface layer is readily controlled. The resulting silver layer is adherent to the surface of the nonconducting substrate. Other features and advantages will be apparent from the following more detailed description of the preferred embodiments, which illustrate, by way of example, the principles of the invention.

DETAILED DESCRIPTION OF THE PREFERRED EMBODIMENTS

In accordance with a preferred aspect of the invention, a process for depositing a uniform thin layer of silver onto the surface of an electrically non-conducting substrate comprises the steps of cleaning the surface in an aqueous cleaning solution; activating the surface In an aqueous activating solution containing at least about 0.001 grams per liter of a salt containing stannous tin ions; depositing silver onto the surface from a deposition solution having a pH of not less than about 8, and containing silver nitrate, a reduction agent selected from the group consisting of formaldehyde, hydrazine sulfate, hydrazine hydroxide, and hypophosphoric acid, in a concentration sufficient to reduce the silver salt to form metallic silver at the surface of the substrate, and a deposition control agent selected from the group consisting of invertose, succinic acid, sodium citrate, sodium acetate, sodium hydroxide, potassium hydroxide, and ammonia in a concentration sufficient to prevent the silver in the solution from precipitating from the solution, and to permit it to deposit upon the surface of the substrate, the step of depositing being accomplished in darkness; and stabilizing the deposited silver by contacting the surface upon which colloidal silver has deposited for at least about 5 seconds with a stabilizing solution of at least about 0.001 grams per liter of a salt of a metal selected from a member of the platinum group and gold dissolved in dilute nitric acid, the resulting solution having a pH value of from about 3.0 to about 4.8.

The present invention is operable in depositing a colloidal metallic silver layer upon the surfaces of many different nonconducting substrate materials. The substrate may itself be a flexible film, or may be a rigid solid. Such materials include, by way of example and not limitation, latex, polystyrene, polyester, polyvinylchloride, polyurethane, ABS polymers, ceramics such as aluminum oxide, glass, polyamide, polyimide, polycarbonate, and synthetic rubber. The nature of the surfaces of these materials varies widely, but the present approach is applicable for all.

It is important that the surface of the substrate be sufficiently clean that it can be wetted by subsequent activation, deposition, and stabilization solutions. Contaminant layers of grease, oil, dirt, chemicals, and other materials can interfere with the ability of these solutions to react with the surface. If the surface is sufficiently clean initially so that wetting can be accomplished, no further cleaning is necessary. However, for many nonconducting substrate materials in commercial applications, cleaning is necessary because the surface has not been sufficiently protected from dirt and organics prior to the silver deposition operation. The surface of such a substrate is preferably cleaned by a technique appropriate to that particular nonconducting material.

For example, polycarbonate, polyamide, polyvinylchloride, polyurethane, and polyester may be cleaned in a 5 percent sodium hydroxide solution at 40° C. for 10 minutes. Polystyrene may be cleaned in a 10 percent sodium hydroxide solution at 30°–40° C. for 5–20 minutes. Latex and synthetic rubber are cleaned in a 3 percent sodium hypochlorite solution at ambient temperature for 1–5 minutes. Ceramics such as aluminum oxide may be cleaned in a 25 percent sulfuric acid solution at 60° C. for 20 minutes, with at least about 5 minutes including simultaneous ultrasonic agitation. Polyimide film may be washed in acetone. Glass is cleaned in an aqueous solution of 0.5 percent hydrofluoric acid and 10 percent sulfuric acid, which imparts a slight etch to the glass. ABS polymer may be cleaned in an aqueous solution containing 350 to 400 grams per liter of chromic acid, and 25 percent sulfuric acid, at 65°–70° C., for 5 to 10 minutes. These cleaning treatments are illustrative and not limiting.

The cleaning, if necessary, is normally accomplished by immersion of the substrate into the cleaning solution, but the cleaner may be sprayed, brushed, or otherwise applied to the surface. If cleaning is required, the surface is thoroughly rinsed in demineralized water after cleaning, but the surface is not dried. At several points in the process as preferably practiced, the substrate surface is rinsed in demineralized (or deionized) water. It is important that this be a thorough rinse, because chemicals transferred from one process step to another may interfere with the subsequent step.

The clean surface of the substrate is activated, also termed sensitized, to prepare it for the deposition step. Activation is accomplished in a dilute activation solution containing at least 0.001, preferably 0.01 to 0.5, most preferably 0.01 to 0.2, grams per liter of a salt containing stannous tin ions. The adjective "stannous" indicates that the tin ions of the salt are in the +2 or (II) oxidation state. Preferred salts are stannous chloride ($SnCl_2$) and stannous fluoride ($SnF_2$). The selected salt is dissolved in acidified demineralized water to form the activation solution. The pH of the solution is preferably from about 1.2 to about 3.5, most preferably about 2.5, attained by adding the required amount of hydrochloric acid. The activation solution is preferably freshly prepared, not stored for more than about 1 day, although the life of the solution is longer for more dilute concentrations.

Treatment of the surface in the activation solution is preferably for about 5–30 minutes at ambient temperature. After the treatment is complete, the surface is removed from the solution and rinsed thoroughly in demineralized water, but not dried.

The activated and rinsed substrate is transferred to the deposition solution. The transfer is preferably done immediately, but tests have shown that the activated substrate may be stored in demineralized water for at least several days. The silver deposition solution is preferably freshly prepared, no more than about four hours prior to use, and has a pH of not less than 8. The deposition solution is preferably not used for too many substrates, as the quality of the deposited film can be reduced if the solution is used too many times. It includes a silver-containing salt, preferably silver nitrate ($AgNO_3$), in an effective amount of no more than about 0.10 grams per liter, preferably about 0.015, grams per liter. If the silver content is above about 0.10 grams per liter, the elemental silver may form nonuniformly, in the solution or on the container walls. Expensive silver may be wasted, because the deposition solution is preferably discarded after 2–3 uses. If the silver content is below an effective amount, there is insufficient silver to form a film in the desired time.

A second component of the deposition solution is a reduction agent that reduces the silver-containing salt to elemental silver. The reduction agent must be present in an amount sufficient to accomplish that chemical reduction. Acceptable reduction agents include formaldehyde, hydrazine sulfate, hydrazine hydroxide, and hypophosphoric acid. It is preferably present in an amount of about 0.001 milliliters per liter of solution. Too large a concentration of the reduction agent causes deposition of silver throughout the solution and on the container walls, while too small a concentration may result in an insufficient formation of metallic silver on the substrate.

Another component of the deposition solution is a deposition control agent that is present in an amount sufficient to slow the deposition reaction to prevent the reduced metallic silver from precipitating directly from solution as a fine metallic powder, or precipitating onto the walls of the container. Operable deposition control agents include inverted sugar, also known as invertose, succinic acid, sodium citrate, sodium acetate, sodium hydroxide, potassium hydroxide, and ammonia. The deposition control agent is preferably present in an amount of about 0.05 grams per liter of solution. If too little is present, the above-described precipitation from solution of metallic silver particles may occur. If too much is present, the silver-containing salt may become too stable for the desired precipitation onto the substrate of interest.

The concentrations of the reduction agent and the deposition control agent may be adjusted as necessary to achieve the desired results, depending upon the substrate material, the thickness of the film desired, the conditions of deposition, and the concentration of silver in the solution. For example, for thin films the silver salt concentration will be relatively low, as will the concentrations of the reduction agent and the deposition control agent.

In preparing the deposition solution, each of the components of the solution is preferably individually dissolved in demineralized water. The various pre-solutions are then mixed, and diluted where necessary, in the correct amounts to achieve the concentrations indicated previously. Mixing the components together during the solution-forming stage may result in instability and precipitation of silver prematurely. If the solution is to be stored before use, it must be stored in darkness to prevent undesired deposition.

The silver salt that is the source of the deposited silver is highly sensitive to decomposition by light in the visible range, and such light is therefore excluded from the deposition procedure. The combination of silver salt and reduction agent, used in darkness, permits the silver to be reduced from the salt in a colloidal state to be deposited upon the surface of the substrate. This colloidal state is particularly beneficial to achieve good adhesion of the completed silver film to the substrate surface, good transparency as a thin film, biocompatibility, tissue friendliness, and non-toxicity. Various of these properties may be important in different applications of the thin film. Good adhesion is important in nearly all uses. Biocompatibility, tissue friendliness, and non-toxicity are particularly important in medical applications. Uniform transparency is critical for electrical instrument requirements.

The substrate surface is exposed to the deposition solution by any appropriate procedure. Dipping into the solution is normally preferred, but the solution may be applied by any convenient technique such as spraying or brushing. The silver film deposits uniformly from the solution at a rate that may be controlled by the concentration of the silver salt. With a concentration of about 0.015 grams per liter of silver nitrate, the deposition rate is about 5 Angstroms per second at ambient temperature, although in some circumstances the rate may be as high as about 7 Angstroms per second at ambient temperature, with the deposition rate increasing with increasing temperature. If a thin film is required, the temperature of deposition is maintained sufficiently low that deposition is controllably slow. Thus, a repeatable, uniform thin film about 50 Angstroms thick may be prepared by immersion for 10 seconds. Increasing the deposition time increases the film thickness proportionately, at least up to thicknesses of about 2000 Angstroms. This relationship between deposition time and film thickness is presented as a guideline, and an actual calibration can be readily obtained for any particular combination of substrate and treatment procedures.

After deposition is complete, the coated substrate is removed from the deposition solution and rinsed in demineralized water, but not dried.

At this point, the silver is present as a metallic deposit upon the treated surface of the substrate. It could be used in this condition for some applications, but is preferably stabilized to avoid chemical and physical changes during use. The metallic silver deposit is stabilized by exposing the surface to a stabilization solution. This solution is prepared by dissolving at least about 0.001, preferably from about 0.001 to about 0.1, and most preferably from about 0.02 to about 0.05, grams per liter of a salt of a platinum group metal (such as platinum, palladium, rhodium, iridium, ruthenium, and osmium) or gold, preferably a platinum salt, into dilute hydrochloric acid. The dilute acid is preferably prepared by boiling conventional concentrated hydrochloric acid to remove water, and then diluting the acid with demineralized water to a pH of from about 3.0 to about 4.8. The stabilization solution should be used within 8 hours of preparation, and is preferably discarded after 2–3 uses. The stabilization solution is contacted to the surface for at least about 5 seconds at ambient temperature, and preferably for 1–20 minutes at ambient temperature.

After the stabilization treatment, the substrate surface is rinsed in demineralized water and dried. It is then ready for use, having an adherent silver coating that is uniformly of a thickness determined by the deposition time. Large numbers of pieces can be coated at a time using this approach, and the places may be of irregular size and shape. Coating is accomplished on the inside of even small bores if the solutions can be contacted to the inside walls. In some instances, it may be necessary to force the various solutions through the small bores to achieve wetting and reaction. Using the technique of the invention, silver has been coated into bores as small as 0.002 millimeters in diameter.

The preceding processing treatment is sensitive to impurities in the solutions. It is therefore preferred that reagent grade chemicals and demineralized (deionized) water be used in all procedures.

The following examples are presented as illustrative of the process of the invention and its results, and should not be taken as limiting of the invention in any respect.

EXAMPLE 1

A uniform layer of silver was deposited on the surface of a polycarbonate substrate. The polycarbonate was first immersed in a 5 percent sodium hydroxide cleaning solution at 40° C. for 10 minutes, followed by a rinsing in demineralized water. The substrate was then activated by immersion in a solution of 0.05 grams per liter of stannous fluoride having a pH of 2.5, at 25° C. for 15 minutes, and rinsed in demineralized water. The surface was then plated with silver by immersion in a freshly prepared deposition solution containing 0.015 grams per liter silver nitrate, 0.05 milliliters per liter ammonia, 0.05 grams per liter sodium citrate, 0.05 grams per liter invertose, and 0.001 milliliters per liter formaldehyde. The deposition step was performed in a dark room at ambient temperature. In one instance, the substrate was immersed for 2 minutes, yielding a silver layer about 500 Angstroms thick. In another instance, the substrate was immersed for 5 minutes, yielding a silver layer about 1200 Angstroms thick. In each case, the substrate was rinsed in demineralized water after deposition was complete. In each case, the deposited silver layer was stabilized by dipping the surface into a stabilization solution of 0.06 grams per liter of gold chloride, at 35° C. for 30 seconds. The stabilized substrate was then rinsed in demineralized water and dried by a jet of compressed air.

EXAMPLES 2–7

The process of claim 1 was repeated, using, as the respective substrates, synthetic rubber, polyester, polyurethane, polyvinylchloride, polystyrene, and polyamide. Deposition was successful in each instance.

EXAMPLE 8

An aluminum oxide substrate was cleaned by immersion at 60° C. for 20 minutes in a cleaning solution of 25 percent concentration sulfuric acid. During 5 of the 20 minutes, the cleaning solution was ultrasonically agitated. The substrate was rinsed in demineralized water. The substrate was then activated by placing it in a freshly prepared activation solution of 0.2 grams per liter stannous chloride, for 15 minutes at ambient temperature, and then rinsed in demineralized water. The substrate was coated with silver by immersing it in the same deposition solution as described for Example 1, except that the time of contact was 20 minutes, and rinsed in demineralized water. The aluminum oxide was then stabilized by immersion in a stabilization solution of 0.01 grams per liter of platinum chloride for 1 minute, followed by a rinse in demineralized water and drying.

EXAMPLE 9

Another aluminum oxide substrate was cleaned by immersion in a 5 percent sodium hydroxide solution at 60° C. for 20 minutes, followed by rinsing in demineralized water containing hydrochloric acid with a pH of 1.5. The substrate was activated by immersing it in a solution of 0.2 grams per liter stannous chloride for 15 minutes at ambient temperature, followed by rinsing in demineralized water. A silver layer was deposited by immersing the substrate, in darkness at 15° C. for 90 seconds, in a deposition solution of 0.01 grams per liter silver nitrate, 0.05 milliliters per liter ammonia, and 0.08 grams per liter sodium citrate. The substrate was washed in demineralized water, and dried. No stabilization treatment was performed for this example. The resulting silver layer was about 350 Angstroms thick.

EXAMPLE 10

A polyimide substrate was cleaned for 5 minutes in acetone at ambient temperature, and then rinsed in demineralized water. It was immersed in a 0.15 grams per liter stannous fluoride activation solution also containing 10 percent acetone, at a temperature of 30° C. for 10 minutes, followed by rinsing in demineralized water. Silver deposition was accomplished as in Example 1, for an immersion time of 5 minutes, followed by rinsing in demineralized water. The coated surface was stabilized in a solution of 0.005 grams per liter of platinum chloride and 0.005 grams per liter of gold chloride, with sufficient hydrochloric acid added to lower the pH to 4.1. The stabilization treatment was at 40° C. for 10 minutes.

EXAMPLE 11

A silver layer was deposited upon the inside and the outside of a catheter made of latex (natural rubber). The latex sheet was cleaned in a cleaning solution containing 1–5 percent of sodium hypochlorite, at ambient temperature for 2 minutes, followed by rinsing in demineralized water. It was placed into an activating solution of 0.05 grams per liter of stannous chloride at ambient temperature for 10 minutes, followed by rinsing in demineralized water. Silver was deposited by placing the latex sheet into a bath containing 0.01 grams per liter of silver nitrate, 0.10–0.12 grams per liter sodium titrate, and sufficient ammonia to achieve a pH of from about 8.5 to about 9.5. The silver layer was stabilized a solution of 0.1 percent platinum chloride in hydrochloric acid to a pH of about 4.1, for a time of 1 minute at ambient temperature.

EXAMPLE 12

A borosilicate glass plate was immersed in a cleaning solution of 0.5 percent hydrofluoric acid with 10 percent sulfuric acid for 5 minutes at ambient temperature, and rinsed thoroughly in demineralized water. It was activated in a 0.01 percent solution of stannous fluoride, and rinsed. It was then dipped into a solution of silver nitrate at 0.05 grams per liter, together with 0.02 percent of hydrazine hydrate reducing agent and sodium hydroxide and ammonia to a pH value of 8.5, for a time of 10 minutes. After rinsing, the substrate was stabilized in an acid solution of 0.05 grams per liter palladium chloride and dried.

EXAMPLE 13

A substrate of ABS plastic polymer was cleaned in a solution of 350 grams per liter of chromic acid and 25 percent sulfuric acid at 67° C. for 5 minutes. After rinsing, the substrate was sprayed with a 0.05 grams per liter solution of stannous chloride, and rinsed. Silver was deposited from a solution of 0.01 grams per liter silver nitrate, 0.05 grams per liter sodium acetate, 0.01 milliliter s per liter hydrazine sulfate, and ammonia to a pH value of 9.0, by immersing the substrate for 5 minutes. The silver film was stabilized in a 0.1 percent acid solution of platinum chloride.

EXAMPLE 14

Eight batches of latex catheters having twenty-five catheters per batch were coated with silver using the approach of Example 11, and then later tested for antimicrobial activity. All catheters showed increased resistance to microbial activity as compared with uncoated latex catheters, indicating that the batch process was successful in attaining a high yield of coated catheters.

EXAMPLE 15

A latex catheter coated with hydrogel was further coated with a silver layer using the procedure of Example 11.

EXAMPLE 16

Example 11 was repeated, and then a hydrogel layer was coated over the silver coating using a conventional dipping procedure.

EXAMPLE 17

A polyurethane catheter was coated with silver using the procedure of Example 1.

EXAMPLE 18

A teflon (polytetrafluoroethylene) coated latex catheter was coated with silver using the procedure of Example 11, after first etching the teflon coating in liquid sodium.

EXAMPLE 19

The interior of a polyethylene bottle was coated with silver using the present approach of Example 1, to provide a barrier coating.

EXAMPLE 20

The adhesion of silver layers on latex specimens, prepared by the present approach of Example 19 and a prior art electrolytic deposition approach, was evaluated qualitatively and quantitatively by several approaches. In one, ultrasonic energy was introduced into the specimen, and increased until the bond between the silver layer and the substrate was weakened to an extent that the silver layer could be removed. The specimen prepared by the present approach withstood four times as much ultrasonic energy as the electrolytically coated specimen before the silver layer could be removed. The interfaces of other specimens was viewed in an electron microscope. In each case the interfaces contained small pores. The pore size for the specimen prepared by the present approach was less than 3 Angstroms, while the pore size for the electrolytically prepared specimen was 15–20 Angstroms. A smaller pore size suggests better interface properties for the specimen prepared by the present approach.

EXAMPLE 21

A number of catheters of different compositions and coatings were prepared. The silver-coated catheters were prepared by the process of the present invention. A 10 square centimeter area of each catheter was placed into a vial containing 5 milliliters of a culture medium. After incubation at 37° C. for 48 hours, the extract was diluted with medium to give final extract concentrations of 5, 25, 50, 75, and 100 percent. Cell monolayers of mouse fibroblast cell line L929 were established in plastic multiwell plates. One milliliter of the cell medium was replaced by the catheter extract from the dilutions. The plates were incubated for an additional 48 hours. The extract concentrations were prepared and assessed in triplicate.

One, hour before termination of the cultures, 1.0 microcuries of $^3$H-thymidine was added to each well. The cells were rinsed with ice-cold 1.5 percent perchloric acid, 0.7 milliliters of 5 percent perchloric acid was added to each well, and the well was heated to 65° C. for 1 hour. After cooling, the fluid was transferred to a scintillation vial and the counts per minute recorded. The results are expressed as the mean percentage of control plotted against extract concentration. The extract concentration which depressed uptake to 50 percent of control, termed $IC_{50}$, was determined for each material. It is known that the higher the $IC_{50}$ value, the least urethral inflammation is produced by a catheter.

The catheter materials and coatings, with the $IC_{50}$ value for each, are: latex, 21.7; silver-coated latex, 71.2; silver nitrate-coated latex, 36.3; silver sulfate-coated latex, 43.8; teflon-coated latex, 55.3; silver-coated teflon, 81.2, silver nitrate-coated teflon, 62.4; silver sulfate-coated teflon, 64.9; silicone, no toxicity; silver-coated silicone, no toxicity; silver nitrate-coated silicone, 66.4; silver sulphate-coated silicone, 75.6. The silver-coated catheter materials are superior in $IC_{50}$ value to uncoated materials and those coated with a silver salt.

EXAMPLE 22

Artificial urine containing *P. aeruginosa* was circulated through catheters made of latex, and latex coated with silver by the approach of Example 11. After up to 10 hours of circulation, disks of each catheter were removed for examination in a scanning electron microscope, after treatment to made the bacteria visible. The visual examination showed that initially neither material had bacterial cells. After 10 minutes of exposure to the artificial urine, the latex specimen showed significant numbers of bacteria, while the silver coated specimen had no observable bacteria. After 10 hours of exposure, the latex disks were completely occluded by adherent bacteria, but there was no colonization on the silver-coated latex disks.

The present invention provides a method to coat various types and configurations of nonconducting substrates with thin layers of silver. These silver layers are beneficially used in medical, optical transmission, and barrier applications, among others. Medical devices such as access devices, lead devices, implants, gloves, condoms, catheters, and wound dressings may be coated. Bottles are coated to provide a gas barrier. Transparent nonconductive substrates are coated with a thin, invisible film of silver to absorb thermal energy. The silver films of the present invention are most advantageously applied in thicknesses of less than that required to be visible to the eye.

The process of the invention thus provides an important improvement to the art of preparing uniform thin films of silver onto nonconducting substrates. The films can be prepared reproducibly in a commercial setting, using dilute, benign wet chemical solutions. Although a particular embodiment of the invention has been described in detail for purposes of illustration, various modifications may be made without departing from the spirit and scope of the invention. Accordingly, the invention is not to be limited except as by the appended claims.

What is claimed is:

1. A method to prepare an antimicrobial medical device, which medical device comprises a nonconducting material having coated on at least a portion of the surface area thereof an adhesive, thin, uniform, transparent, antimicrobial, biocompatible coating consisting essentially of silver metal in combination with one or more platinum group metal or gold metal or both platinum group metal and gold metal, which method comprises (a) activating said portion of the surface area; followed by
   (b) chemically depositing said coating by treating said activated surface with an aqueous solution of at least one salt of silver in the presence of a deposition control agent; followed by
   (c) treating with a solution of a salt of said platinum group metal or gold or both,
      all in the absence of an electric current, said depositing being conducted for only sufficient time to result in said thin transparent coating; followed by
   (d) rinsing said coating in demineralized water and drying said coating.

2. The method of claim 1 wherein said depositing is conducted in the absence of a reducing agent.

3. The method of claim 1 wherein said activating is conducted by treating said surface area portion with a solution of stannous ion.

4. The method of claim 3 wherein the concentration of said stannous ion in solution corresponds to about 0.1–0.5 grams per liter of stannous chloride.

5. The method of claim 1 wherein said deposition control agent is selected from the group consisting of sodium citrate, sodium acetate, sodium hydroxide, potassium hydroxide, ammonia and a combination of one or more of the foregoing.

6. The method of claim 1 wherein said surface area portion is treated with an activating solution of stannous chloride followed by washing, followed by treating with an aqueous solution of silver nitrate containing at least one deposition control agent, followed by treating with a solution of a salt of a platinum group metal ion or gold or both platinum group metal ion and gold ion.

7. The method of claim 1 which further comprises treating said coated portion with a hydrogel layer.

8. The method of claim 1 wherein said platinum group metal is platinum or palladium.

9. The method of claim 8 wherein said platinum group metal is in combination with gold.

10. The method set forth in claim 1 wherein said step of treating with a solution of a salt of said platinum group metal or gold or both is conducted at room temperature.

11. A method to prepare an antimicrobial medical device, which medical device comprises a nonconducting material having coated on at least a portion of the surface area thereof an adhesive, thin, uniform, antimicrobial, biocompatible coating consisting essentially of silver metal in combination with one or more platinum group metal or gold metal or both platinum group metal and gold metal, which method comprises
  (a) activating said portion of the surface area; followed by
  (b) chemically depositing said coating by treating said activated surface with an aqueous solution of at least one salt of silver in the presence of a deposition control agent; followed by
  (c) treating with a solution of a salt of said platinum group metal or gold or both,
    all in the absence of an electric current, said depositing being conducted for only sufficient time to result in said thin coating; followed by
  (d) rinsing said coating in demineralized water and drying said coating.

12. The method of claim 11 wherein said depositing is conducted in the absence of a reducing agent.

13. The method of claim 11 wherein said activating is conducted by treating said surface area portion with a solution of stannous ion.

14. The method of claim 13 wherein the concentration of said stannous ion in solution corresponds to about 0.1–0.5 grams per liter of stannous chloride.

15. The method of claim 11 wherein said deposition control agent is selected from the group consisting of sodium citrate, sodium acetate, sodium hydroxide, potassium hydroxide, ammonia and a combination of one or more of the foregoing.

16. The method of claim 11 wherein said surface area portion is treated with an activating solution of stannous chloride followed by washing, followed by treating with an aqueous solution of silver nitrate containing at least one deposition control agent, followed by treating with a solution of a salt of a platinum group metal ion or gold or both platinum group metal ion and gold ion.

17. The method of claim 11 which further comprises treating said coated portion with a hydrogel layer.

18. The method of claim 11 wherein said platinum group metal is platinum or palladium.

19. The method of claim 18 wherein said platinum group metal is in combination with gold.

20. The method set forth in claim 11 wherein said step of treating with a solution of a salt of said platinum group metal or gold or both is conducted at room temperature.

* * * * *